US009790305B2

(12) United States Patent
Mehl et al.

(10) Patent No.: US 9,790,305 B2
(45) Date of Patent: Oct. 17, 2017

(54) SITE SPECIFICALLY INCORPORATED INITIATOR FOR GROWTH OF POLYMERS FROM PROTEINS

(71) Applicant: Franklin and Marshall College, Lancaster, PA (US)

(72) Inventors: Ryan A. Mehl, Corvalli, OR (US); Krzysztof Matyjaszewski, Pittsburgh, PA (US); Saadyah Averick, Pittsburgh, PA (US)

(73) Assignee: Franklin and Marshall College, Lancaster, PA (US)

(*) Notice: Subject to any disclaimer, the term of this patent is extended or adjusted under 35 U.S.C. 154(b) by 469 days.

(21) Appl. No.: 13/837,590

(22) Filed: Mar. 15, 2013

(65) Prior Publication Data
US 2014/0004591 A1 Jan. 2, 2014
US 2016/0251467 A9 Sep. 1, 2016

Related U.S. Application Data

(63) Continuation-in-part of application No. 13/788,710, filed on Mar. 7, 2013, now Pat. No. 8,816,001, which is a continuation of application No. PCT/US2011/051043, filed on Sep. 9, 2011.

(60) Provisional application No. 61/613,178, filed on Mar. 20, 2012.

(51) Int. Cl.
A61K 47/48 (2006.01)
C08F 220/26 (2006.01)
C07C 69/00 (2006.01)
C12N 9/96 (2006.01)

(52) U.S. Cl.
CPC .............. C08F 220/26 (2013.01); C12N 9/96 (2013.01); A61K 47/4823 (2013.01)

(58) Field of Classification Search
CPC ..... C12P 21/02; C12N 11/08; C12N 2533/30; C12N 11/06
USPC ................................................ 435/180, 188
See application file for complete search history.

(56) References Cited

U.S. PATENT DOCUMENTS

| 4,033,998 | A | 7/1977 | Harris |
| 5,763,546 | A | 6/1998 | Jung et al. |
| 5,789,487 | A | 8/1998 | Matyjaszewski et al. |
| 5,807,937 | A | 9/1998 | Matyjaszewski et al. |
| 5,945,491 | A | 8/1999 | Matyjaszewski et al. |
| 6,111,022 | A | 8/2000 | Matyjaszewski et al. |
| 6,121,371 | A | 9/2000 | Matyjaszewski et al. |
| 6,124,411 | A | 9/2000 | Matyjaszewski et al. |
| 6,162,882 | A | 12/2000 | Matyjaszewski et al. |
| 6,197,794 | B1 | 3/2001 | Head et al. |
| 6,407,187 | B1 | 6/2002 | Matyjaszewski et al. |
| 6,492,421 | B1 | 12/2002 | Thorsett et al. |
| 6,512,060 | B1 | 1/2003 | Matyjaszewski et al. |
| 6,538,091 | B1 | 3/2003 | Matyjaszewski et al. |
| 6,541,580 | B1 | 4/2003 | Matyjaszewski et al. |
| 6,624,262 | B2 | 9/2003 | Matyjaszewski et al. |
| 6,627,314 | B2 | 9/2003 | Matyjaszewski et al. |
| 6,759,491 | B2 | 7/2004 | Matyjaszewski et al. |
| 6,790,919 | B2 | 9/2004 | Matyjaszewski et al. |
| 6,887,962 | B2 | 5/2005 | Matyjaszewski et al. |
| 7,019,082 | B2 | 3/2006 | Matyjaszewski et al. |
| 7,049,373 | B2 | 5/2006 | Matyjaszewski et al. |
| 7,064,166 | B2 | 6/2006 | Matyjaszewski et al. |
| 7,125,938 | B2 | 10/2006 | Matyjaszewski et al. |
| 7,157,530 | B2 | 1/2007 | Matyjaszewski et al. |
| 7,332,550 | B2 | 2/2008 | Matyjaszewski et al. |
| 7,825,199 | B1 | 11/2010 | Matyjaszewski et al. |
| 8,273,823 | B2 | 9/2012 | Matyjaszewski et al. |
| 8,497,356 | B2* | 7/2013 | Chilkoti ........... A61K 47/48215 530/350 |
| 2004/0110753 | A1 | 6/2004 | Jackson et al. |
| 2004/0158076 | A1 | 8/2004 | Jackson et al. |
| 2005/0283021 | A1 | 12/2005 | Hamada et al. |
| 2007/0123646 | A1 | 5/2007 | Lele et al. |
| 2011/0294189 | A1* | 12/2011 | Chilkoti ............... C07K 1/1075 435/188 |

FOREIGN PATENT DOCUMENTS

| DK | WO2005014049 | * | 2/2005 |
| WO | 2004087777 | A2 | 10/2004 |
| WO | 2005087818 | A1 | 9/2005 |
| WO | 2005087819 | A1 | 9/2005 |
| WO | 2007025086 | A2 | 3/2007 |
| WO | 2007075817 | A1 | 7/2007 |
| WO | 2008148000 | A1 | 12/2008 |
| WO | 2012034043 | A1 | 3/2012 |
| WO | 2012054700 | A1 | 4/2012 |

OTHER PUBLICATIONS

Peeler et al. JACS, 2010,132, pp. 13575-13577.*
Averick et al. Polymer Chem. 2011, 2, pp. 1476-1478.*
Xu et al. Biomacromolecule 2010, 11 pp. 1810-1817.*
Gupta et al. Chem. Commun 2005, pp. 4315-4317.*
Broyer et al. Chem. Commun. 2011, 47, pp. 2212-2226.*
PCT Notification of Transmittal of the International Search Report and the Written Opinion of the International Searching Authority, or the Declaration, dated Jan. 26, 2012, 6 pages.
Gao W., Liu W., Mackay J. A., Zalutsky M. R., Toone E. J. Chilkoti A., In situ growth of a stoichiometric PEG-like conjugate at a protein's N-terminus with significantly improved pharmacokinetics, PNAS, Sep. 8, 2009, vol. 106, No. 36, 15231-15236.
Hong J., Gong P., Xu D., Dong L., Yao S., Stabilization of __ chymotrypsin by covalent immobilization on amine-functionalized superparamagnetic nanogel, Journal of Biotechnology 128 (2007) 597-605.
Harris, J. M., Chess R. B., Effect of Pegylation on Pharmaceuticals, www.nature.com/reviews/drugdisc, Mar. 2003, vol. 2.
Duncan R., The Dawning Era of Polymer Therapeutics, Nature Reviews, Drug Discovery, vol. 2, May 2003, 347.

(Continued)

Primary Examiner — Robert Mondesi
Assistant Examiner — Md. Younus Meah
(74) Attorney, Agent, or Firm — Barley Snyder

(57) ABSTRACT

The present invention is directed towards a protein-polymer composition having a protein with a site-specifically incorporated unnatural amino acid initiator and a covalently attached polymer.

36 Claims, 9 Drawing Sheets

(56) References Cited

OTHER PUBLICATIONS

Nicolas J., Mantovani G., Haddleton D., M. Living Radical Polymerization as a Tool for the Synthesis of Polymer-Protein/Peptide Bioconjugates, Macromol. Rapid Commun, 2007, 28, 1083-1111.
Liu J., Bulmus V., Herlambang D. L., Barner-Kowollik C., Stenzel M. H., Davis T. P., In Situ Formation of Protein-Polymer Conjugates through Reversible Addition Fragmentation Chain Transfer Polymerization, Angew. Chem. It., Ed. 2007, 46, 3099-3103.
Le Droumaguet B., Velonia K., In Situ ATRP-Mediated Hierarchical Formation of Giant Amphiphile Bionanoreactors, Angew. Chem. Int. Ed. 2008, 47, 6263-6266.
Krishna P. D., Kiick K. L., Invited Review Protein- and Peptide-Modified Synthetic Polymeric Biomaterials, PeptideScience, vol. 94, No. 1.
Borner, H. G., Kuhnle H., Hentschel J., Making "Smart Polymers" Smarter: Modern Concepts to Regulate Functions in Polymer Science, Highlight, J. Polym. Sci. Part A: Polym Chem.: vol. 48 (2010).
Conner, R. E., Tirrell D. A., Non-Canonical Amino Acids in Protein Polymer Design, 2007, Polymer Reviews, 47:1, 9-28.
Zeng, Q., Li T., Cash B., Li S., Xie F., Wang Q., Chemoselective derivatization of a bionanoparticle by click reaction and ATRP reaction, Chem. Commun., 2007, 1453-1455.
Canalle L. A., Lowik D. W. P. M., Hest, J. C. M., Polypeptide-polymer bioconjugates, Chem. Soc. Rev., 2010, 39, 329-353.
Lele B. S., Murata H., Matyjaszewski K., Russell A. J., Synthesis of Uniform Protein-Polymer Conjugates, Biomacromolecules 2005, 6, 3380-3387.
Yan M., Liu Z., Lu D., Liu Z., Fabrication of Single Carbonic Anhydrase Nanogel against Denaturation and Aggregation at High Temperature, Biomacromolucules 2007, 8, 560-565.
Ge J., Lu D., Wang J. Liu Z., Lipase Nanogel Catalyzed Transesterification in Anhydrous Dimetryl Sulfoxide, Biomacromolucles 2009, 10, 1612-1618.
Ito, Y., Fujii H., Imanishi Y., Modification of Lipase with Various Synthetic Polymers and Their Catalytic Activities in Organic Solvent, Biotechnol. Prog. 1994, 10, 398-402.
Matyjaszewski K., Zia J., Atom Transfer Radical Polymerization, Chem. Rev. 2001, 2921-2990.
Wang J. S., Matyjawzewski K., Controlled/"Living" Radical Polymerization. Atom Transfer Radical Polymerization in the Presence of Transition-Metal Complexes, J. Am. Chem. Soc. 1995, 117, 5614-5615.
Heredia K. L., Bontempo D., Ly T. Byers J. T., Halstenberg S., Maynard H. D., In Situ Preparation of Protein—"Smart" Polymer Conjugates with Retention of Bioactivity, J. Am. Chem. Soc. 2005, 127, 16955-16960.
Yan M., Ge J., Liu Z., Ouyang P., Encapsulation of Single Enzyme in Nanogel with Enhanced Biocatalytic Activity and Stability, J. Am. Chem. Soc. 2006, 128, 11008-11009.
Broyer R. M., Quaker G., M., Maynard H. D., Designed Amino Acid ATRP Initiators for the Synthesis of Biohybrid Materials, J. Am. Chem. Soc., 2008, 130, 1041-1047.
Ge J., Lu D., Wang J. Yan M. Lu Y., Liu Z., Molecular Fundamentals of Enzyme Nanogels, J. Phys. Chem. B 2008, 112, 14319-14324.
Averick S., Simakova A., Park S., Konkolewisz D., Magenau A. J. D., Mehl R. A., Matyjaszewski K., ATRP under Biologically Relevant Conditions: Grafting from a Protein, ACS Macro Lett., 2012, 1, 6-10.
Stokes, A. L., Miyake-Stoner S. J., Peeler J. C., Nguyen D. P., Hammer R. P., Mehl R. A., Enhancing the utility of unnatural amino acid synthetases by manipulating broad substrate specificity, Mol. BioSyst., 2009, 5, 1032-1038.
Qiu J., Charleux B., Matyjaszewski K., Controlled/living radical polymerization in aqueous media: homogeneous and heterogeneous systems, Prog. Polym. Sci. 26 (2001) 2083-2134.
Davis K. A., Matyjaszewski K., Statistical, Gradient, Block, and Graft Copolymers by Controlled/ Living Radical Polymerizations, Advances in Polymer Science, vol. 159 @ Springer-Verlag Berlin Heidelberg 2002.
Depp, V., Alikhani A., Grammer V., Lele B. S., Native protein-initiated ATRP: A viable and potentially superior alternative to PEGylation for stabilizing biologics, Acta Biomaterialia 5 (2009) 560-569.
Averick, S. E., Magenau, A. J. D., Simakova, A., Woodman, B. F., Seong A., Mehl R., Matyjeszewski K., Covalently incorporated protein-nanogels using AGET ATRP in an inverse miniemulsion, Polym. Chem., 2011, 2, 1476-1478.
Averick, S. E., Magenau, A. J. D., Simakova, A., Woodman, B. F., Seong A., Mehl R., Matyjeszewski K., Supplementary Material (ESI) for Polymer Chemistry: Covalently incorporated protein-nanogels using AGET ATRP in an inverse miniemulsion, Polym. Chem., 2011, 2, 1476-1478.
Lutz, J., Borner, H. G., Modern trends in polymer bioconjugates design, Prog. Polym. Sci. 33 (2008) 1-39.
Miyake-Stoner, S. J., Miller, A. M., Hammill, J. T., Peller, J. C., Hess, K. R., Mehl, R. A., Brewer, S. H., Probing Protein Folding Using Site-Specifically Encoded Unnatural Amino Acids as FRET Donors with Tryptophan, Biochemistry 2009, 48, 5953-5962.
Miyake-Stoner, S. J., Refakis, C. A., Hammill, J. R., Lusic, H., Hazen, J. L., Deiters A., Mehl, R. A., Generating Permissive Site-Specific Unnatural Aminoacyl-tRNA Synthetases, Biochemistry 2010, 49, 1667-1677.
Boyer, C., Bulmus V., Davis, T. P., Ladmiral V., Liu J., Perrier S., Bioapplications of RAFT Polymerization, Chem. Rev. 2009, 109, 5402-5436.
Matyjaszewski K., Tsarevsky N. V., Nanostrauctured functional materaisl prepared by atom transfer radical polymerization, Nature Chemistry, vol. 1, Jul. 2009.
Pedelacq J-D., Cabantous S., Tran T., Terwilliger T. C., Waldo G. S., Engineering and characterization of a superfolder green fluorescent protein, Nature Biotechnology, vol. 24, No. 1, Jan. 2006.

\* cited by examiner

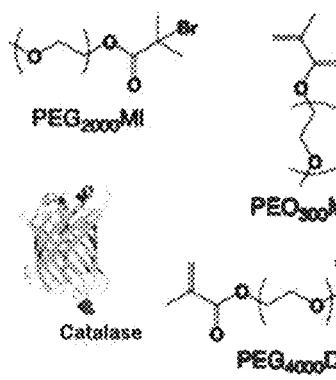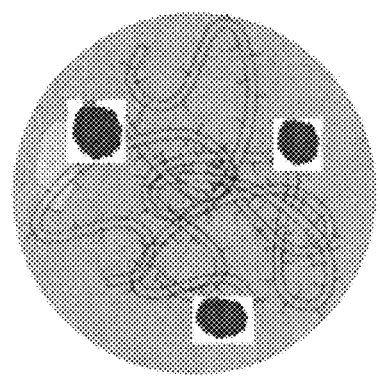
FIG. 2

FIG. 3.1
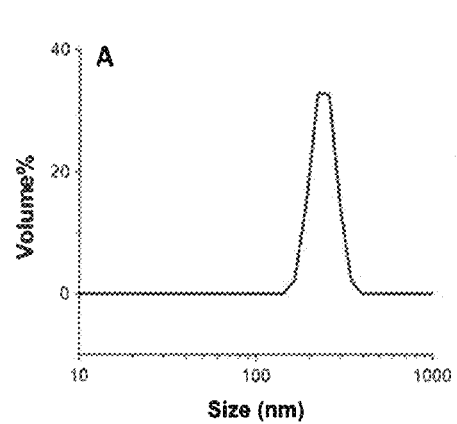
FIG. 3.2
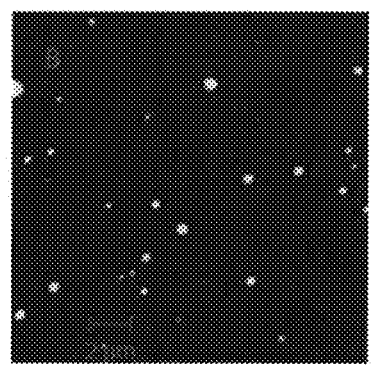

Catalase-NG, Before and After H2O2 addition

FIG. 9.1 FIG. 9.2

SITE SPECIFICALLY INCORPORATED INITIATOR FOR GROWTH OF POLYMERS FROM PROTEINS

CROSS-REFERENCE TO RELATED APPLICATIONS

This application claims benefit of the filing date under 35 U.S.C. §119(a)-(d) of U.S. Provisional Patent Application No. 61/613,178, filed Mar. 20, 2012, and is also a continuation-in-part of U.S. patent application Ser. No. 13/788,710, filed Mar. 7, 2013, which in turn is a continuation of PCT International Application No. PCT/US2011/051043, filed Sep. 9, 2011, which in turn claims priority to U.S. Provisional Application No. 61/381,757, filed Sep. 10, 2010.

INCORPORATION BY REFERENCE

Provisional application 61/381,757 filed on Sep. 10, 2010 is hereby incorporated by reference. PCT application PCT/US2011/51043 filed on Sep. 9, 2011 is also hereby incorporated by reference.

GOVERNMENTAL INTEREST

Some of the work involved in the development described in the invention described in this patent application was partially funded by the National Science Foundation grant DMR-09-69301.

FIELD OF THE INVENTION

The present invention is directed towards a protein-polymer composition having a site-specifically incorporated unnatural amino acid initiator and a covalently attached polymer, and a general method for producing the composition through controlled radical polymerization.

BACKGROUND

Protein-polymer hybrids have revolutionized the treatment of disease [*Chemical Reviews*, 2009, 109, 5402-5436; *Nat Rev Drug Discov*, 2003, 2, 347-360] and biocatalytic processes. [*J. Am. Chem. Soc.*, 2006, 128, 11008-11009]. Protein-polymer hybrids typically comprise linear or branched polymers "grafted to" or "grafted from" accessable sites within the desired protein. These protein-polymer hybrids have already shown an impressive range of altered or improved properties. From a therapeutic perspective, the advantages of protein-polymer hybrids over native proteins include increased in vivo stability, minimized immune recognition due to steric effects, enhanced in vivo circulation, and improved therapeutic effects. Protein-polymer hybrids have also shown an increased solubility in non-aqueous media, which have expanded the utility of enzymatic biocatalytic processes into the realm of organic synthesis. [*Biomacromolecules*, 2009, 10, 1612-1618; *Biotechnology Progress*, 1994, 10, 398-402]

Recently, the concept of protein-polymer nanogel hybrids has been introduced in order to overcome some of the long-term stability issues associated with protein-polymer hybrids. [*J. Am. Chem. Soc.* 2006, 128, 11008-11009; *J. Phys. Chem. B*, 2008, 112, 14319-14324; J. Biotechnology 2007, 128, 597-605.] Some of these issues include organic solvent solubility and deactivation of traditional protein-polymer hybrids under harsh conditions. Both of these characteristics are extremely important for expanding the catalytic potential of enzymatic systems. Encapsulation of proteins into nanogel matrices have demonstrated superior temperature and organic solvent stability for several systems, such as carbonic anhydrase, lipase, and horseradish peroxidase among others. [*Biomacromolecules*, 2007, 8, 560-565 and 2009, 10, 1612-1618; *J. Am. Chem. Soc.* 2006, 128, 11008-11009; *Angew. Chem., Int. Ed*, 2008, 47, 6263-6266]

Traditionally, protein-polymer hybrids are synthesized in a two-step process. The proteins are first functionalized with N-hydroxysuccinimide-acrylate and then copolymerized with an acrylamide and a crosslinker using REDOX initiated free radical polymerization. However, this process produces uncontrolled, non-specific acrylate functionalization of the protein, and often leads to batch-to-batch variability of protein activity. This variability often originates from non-specific modification of lysine residues by the acrylate chemistry, resulting in deactivation of active sites and protein denaturing. [*Nat Rev Drug Discov*, 2003, 2, 214-221] Additionally, the polymers accessible through REDOX initiated free radical polymerizations are limited by a number of factors, including monomer selection, particle size, protein loading, and potential for controlled release properties.

More recently, protein-polymer hybrids have been prepared using controlled radical polymerization techniques (see Wang et al., *Am. Chem. Soc.* 1995, 117, 5614; Matyjaszewski & Xia, *Chem. Rev.* 2001, 101, 2921 ("Xie"); Matyjaszewski &Tsarevsky, *Nature Chem.* 2009, 1, 276) which allow unprecedented control over polymer dimensions (molecular weight), uniformity (polydispersity), topology (geometry), composition and chemical functionality. [Matyjaszewski, K., Ed, Controlled Radical Polymerization; ACS: Washington, D.C., 1998; ACS Symposium Series 685. Matyjaszewski, K., Ed.; Controlled/living Radical Polymerization. Progress in ATRP, NMP, and RAFT; ACS: Washington, D.C., 2000; ACS Symposium Series 768; Matyjaszewski, K., Davis, T. P., Eds. Handbook of Radical Polymerization; Wiley: Hoboken, 2002; Qiu, J.; Charleux, B.; Matyjaszewski, K. *Prog. Polym. Sci.* 2001, 26, 2083; Davis, K. A.; Matyjaszewski, K. *Adv. Polym. Sci.* 2002, 159, 1.]

While controlled radical polymerization techniques permit greater control over the polymer's composition, there is still a need for methods to attach those polymers to site-specific locations on a protein. Thus far, methods for site-specific incorporation of polymerization initiators into proteins have been limited to the N-terminal position or specific natural amino-acid directed linkages. Both of these suffer from challenging purification of intermediates and/or the inability to efficiently control the number or location of potential polymer connections, both of which can compromise the structural integrity of the modified protein.

While the many experiments conducted using in situ functionalized natural amino acids on proteins have illustrated the potential immense impact of well-defined protein-polymer hybrids, their application is limited by technical shortcomings, and there is a need to develop protein polymer hybrids where a desired polymer can be attached at a site-specific location on the protein. [See Broyer et al., *J. Am. Chem. Soc.* 2008, 130, 1041]

SUMMARY

In view of the above-mentioned need, a protein-polymer composition is provided. The protein-polymer composition includes a protein with a site-specifically incorporated unnatural amino acid with a covalently attached polymer.

BRIEF DESCRIPTION OF THE DRAWINGS

Embodiments of the invention will be understood by reference to the following figures, wherein:

FIG. 2: Formation of a catalase protein-nanogel particle in an inverse miniemulsion (Synthetic Scheme 1).

FIG. 3: A) FIG. 3.1 Dynamic light scattering of GFP-1 peak size ~240 nm. B) FIG. 3.2 confocal microscopy of GFP-1.

FIG. 9: Shows expression levels of GTP-wt from pBad-GFP-His6 (Synthetic Scheme 3).

DETAILED DESCRIPTION OF THE EMBODIMENT(S)

Figure 1:
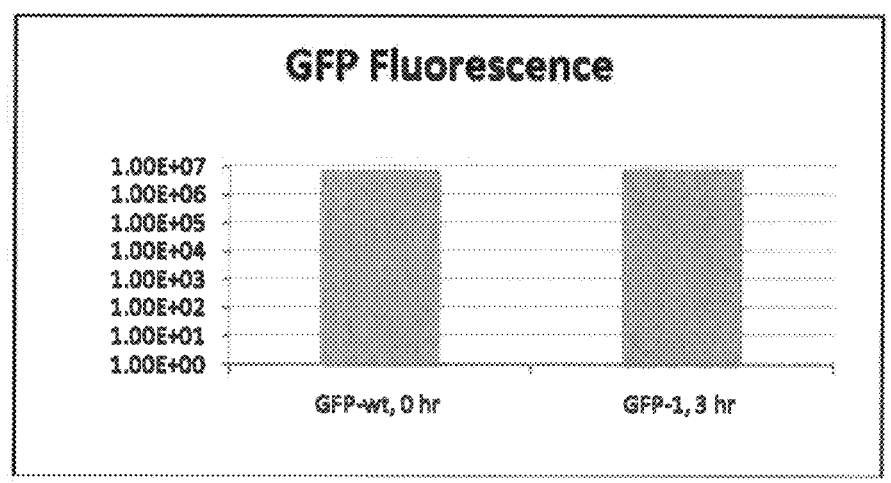
FIG. 1: Shows the emission spectra for GFP-wt and GFP-1-p(OEO300MA) ~510 nm

One aspect of the invention is a protein-polymer composition having a protein with a site-specifically incorporated unnatural amino acid with a covalently attached polymer.

The general method of preparing a protein with a site-specifically incorporated unnatural amino acid is disclosed by Mehl et al., PCT/US2011/57043, and is incorporated herein by reference.

A "protein" (or portion thereof) is understood to include native proteins, as well as proteins that have one or more site-specifically incorporated unnatural amino acids further comprising an initiator for a CRP. No attempt is made to identify the hundreds of thousands of known proteins, any of which may be modified to include one or more unnatural amino acid initiators, e.g., by tailoring any available mutation methods to include one or more appropriate selector codon in a relevant translation system. Common sequence repositories for known proteins include GenBank, EMBL, DDBJ, and the NCBI, among others. Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they can comprise one or more unnatural amino acid initiators. Essentially any protein of interest can be modified to include an initiator comprising an unnatural amino acid initiator.

Proteins are also understood to include enzymes (e.g., therapeutic, diagnostic, or industrial enzymes), or portions thereof with at least one or more unnatural amino acid initiators are also provided by the invention. Examples of enzymes include, but are not limited to, e.g., amidases, amino acid racemases, acylases, dehalogenases, dioxy-genases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminases, and nucleases.

The term "selector codon" refers to a codon recognized by the O-tRNA in the translation process and not typically recognized by an endogenous tRNA. The O-tRNA anticodon loop recognizes the selector codon on the mRNA and incorporates its amino acid, e.g., an initiator amino acid, at this site in the polypeptide. Selector codons can include, e.g., nonsense codons, such as stop codons (e.g., amber, ochre, and opal codons), four or more base codons, rare codons, codons derived from natural or unnatural base pairs, or the like.

The term "translation system" refers to the components that incorporate an amino acid into a growing polypeptide chain (protein). Components of a translation system can include, e.g., ribosomes, tRNAs, synthetases, mRNA, and the like. Typical translation systems include cells, such as bacterial cells (e.g., *Escherichia coli*), archeaebacterial cells, eukaryotic cells (e.g., yeast cells, mammalian cells, plant cells, insect cells), or the like. Alternatively, the translation system comprises an in vitro translation system, e.g., a translation extract including a cellular extract. The O-tRNA or the O-RSs of the invention can be added to or be part of an in vitro or in vivo translation system, e.g., in an eukaryotic cell, e.g., a bacterium (such as *E. coli*), or in a eukaryotic cell, e.g., a yeast cell, a mammalian cell, a plant cell, an algae cell, a fungus cell, an insect cell, or the like. The translation system can also be a cell-free system, e.g., any of a variety of commercially available in vitro transcription/translation systems in combination with an O-tRNA/O-RS pair and an initiator amino acid as described herein.

The translation system may optionally include multiple O-tRNA/O-RS pairs, which allow incorporation of more than one unnatural amino acid, e.g., an initiator amino acid and another unnatural amino acid. For example, the cell can further include an additional different O-tRNA/O-RS pair and a second unnatural amino acid, where this additional O-tRNA recognizes a second selector codon and this additional O-RS preferentially aminoacylates the O-tRNA with the second unnatural amino acid. For example, a cell that includes an O-tRNA/O-RS pair (where the O-tRNA recognizes, e.g., an amber selector codon) can further comprise a second orthogonal pair, where the second O-tRNA recognizes a different selector codon (e.g., an opal codon, four-base codon, or the like). Desirably, the different orthogonal pairs are derived from different sources, which can facilitate recognition of different selector codons.

An "unnatural amino acid" is, in this case a molecule containing a primary amine functionality and carboxylic acid functionality that can be incorporated into a protein primary sequence with a transferable atom or group that is completely incorporated into the final product.

Figure 6:
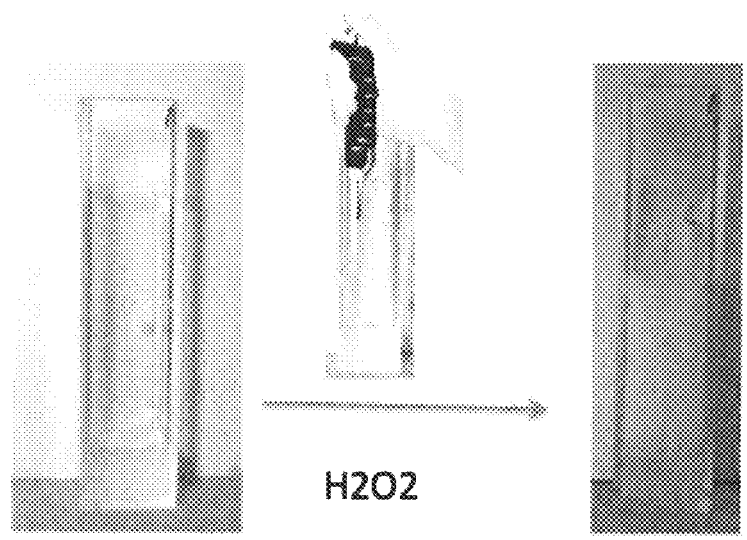
FIG. 6: Shows IMAGE 1, a Catalase-NG, before and after $H_2O_2$ addition, bioengineered to possess 4 ATRP initiating groups.
Figure 7:
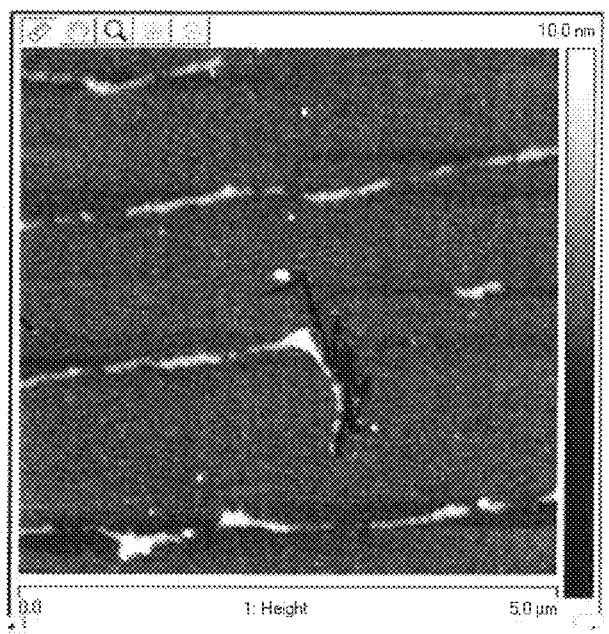
FIG. 7: Shows IMAGE 2, an AFM of a sample of p(GFP-2-PEO$_{lk}$dialkyne) cast at an angle on the surface of mica where a long fiber-like material had formed.

In an embodiment, the unnatural amino acid is site-specifically incorporated into the protein one to five times. In another exemplary embodiment, the unnatural amino acid is site-specifically incorporated into a protein one to three times. In yet another exemplary embodiment, the unnatural amino acid is site-specifically incorporated into a protein one to two times. Exemplary examples include GFP-1, discussed below, wherein a single unnatural amino acid with a covalently attached polymer was incorporated without loss of fluorescence. FIG. 1. In another exemplary example, incorporation of Catalase-NG with four incorporated initiation sites into a nanogel was accomplished while retaining the ability of Catalase to reduce hydrogen peroxide. FIG. 2 and Image 1, FIG. 6.

As used herein, the term "nanogel" refers to a polymer network dispersion capable of absorbing a fluid and retaining at least a portion of the fluid to form a swollen polymer particle. A nanogel can have many sizes, and these sizes are indicative of the nanogel in solvent swollen form.

In an exemplary embodiment, the site specifically incorporated unnatural amino acid is an initiator for a controlled radical polymerization reaction ("CRP"). CRP reactions include, but are not limited to, atom transfer radical polymerization ("ATRP"), nitroxide mediated polymerization ("NMP"), and reversible addition fragmentation transfer ("RAFT") systems. CRP reactions allow unprecedented control over polymer dimensions (molecular weight), uniformity (polydispersity), topology (geometry), composition and functionality. [Matyjaszewski, K., Davis, T. P., Eds. Handbook of Radical Polymerization; Wiley; Hoboken, 2002; Qiu, J.; Charleux, B.; Matyjaszewski, K. *Prog. Polym. Sci*, 2001, 26, 2083; Davis, K. A.; Matyjaszewski, K. *Adv. Polym. Sci*, 2002, 159, 1.]

Matyjaszewski and coworkers disclosed the fundamental four component Atom Transfer Radical Polymerization (ATRP) process comprising the addition, or in situ formation, of an initiator, in this case a molecule with a transferable atom or group that is completely incorporated into the final product, a transition metal and a ligand that form, a partially soluble transition metal complex that participates in a reversible redox reaction with the added initiator or a dormant polymer to form the active species to copolymerize radically polymerizable monomers, and a number of improvements to the basic ATRP process, in a number of patents and patent applications: U.S. Pat. Nos. 5,763,546; 5,807,937; 5,789,487; 5,945,491; 6,111,022; 6,121,371; 6,124,411; 6,162,882; 6,624,262; 6,407,187; 6,512,060; 6,538,091; 6,541,580; 6,624,262; 6,627,314; 6,759,491; 6,790,919; 6,887,962; 7,019,082; 7,049,373; 7,064,166; 7,125,938; 7,157,530; 7,332,550 and U.S. patent application Ser. Nos. 09/534,827; PCT/US04/09905; PCT/US05/007264; PCT/US05/007265; PCT/US06/33152; PCT/US2006/048656 and PCT/US08/64710, all of which are herein incorporated by reference to provide both background and definitions for the terms used herein. Papers include Wang et al., *Am. Chem. Soc.* 1995, 117, 5614; Matyjaszewski & Xia, *Chem. Rev.* 2001, 101, 2921; Matyjaszewski & Tsarevsky, *Nature Chem.* 2009, 1, 276.

In an exemplary embodiment, the unnatural amino acid is an initiator for ATRP, therefore allowing for monomers and cross-linkers to be incorporated in a predictable, controlled, and programmed manner to yield polymer chains of essentially equal length, as defined by the ratio of consumed monomer to the added initiator. Moreover, the functionality present on the introduced initiator can be preserved, including both the α- and ω-chain end functionality on the formed polymer segment. The polymers synthesized using ATRP also may allow many functional groups, such as hydroxyl, amino, amido, esters, carboxylic acid, to be incorporated into a copolymer for use in post-polymerization modifications, including covalent linking of biomolecules for drug delivery. As disclosed below, this enables formation of protein-polymer hybrids between synthetic polymers and biomolecules, and provides delivery systems with customizable and tunable polymer structures for many applications, including but not limited to precise targeted delivery of biologically active molecules.

An "initiator" is understood to mean a chemical species with a transferable atom that is capable of interacting with a transition metal and a ligand to form a partially soluble transition metal complex that participates in a reversible redox reaction with the added initiator or a dormant polymer to form the active species to copolymerize radically polymerizable monomers.

An exemplary embodiment, the unnatural amino acid is represented by formula 2:

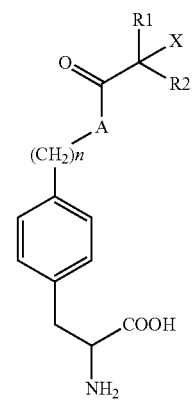

wherein R1 and R2 are independently H, C1-C8 alkyl, cycloalkyl, heterocycloalkyl, aryl, or heteroaryl; X is F, Cl, Br, I, $N_3$, alkoxyamine, or a thiocarbonyl thio moiety; A is O, S, or NR, wherein R is H, C1-C8 alkyl, cycloalkyl, heterocycloalkyl, aryl, or heteroaryl; and as is 0, 1, 2, or 3; or a salt thereof.

In another exemplary embodiment, the unnatural amino acid is represented by formula 1:

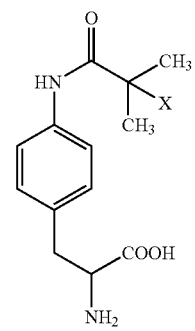

wherein X is F, Cl, Br, I, or —$N_3$, or a salt thereof. In another embodiment, the unnatural amino acid is represented by formula 1, wherein X is Br or Cl, or a salt thereof. In yet another embodiment, the unnatural amino acid is represented by formula 1, wherein X is —$N_3$ or a salt thereof.

In another embodiment, the protein-polymer composition has a polymer with repeating units from a monomer class including methacrylates, acrylates, acrylamides, styrenics, or acrylamide-styrenics, or combinations thereof.

Another aspect of the invention is that the polymer in the protein-polymer composition can include a copolymer that has repeating units from a monomer class including methacrylates, acrylates, acrylamides, styrenics, or acrylamide-styrenics, or combinations thereof.

In yet another embodiment, the polymer may be copolymerized with difunctional monomers.

In yet another embodiment, when the polymer is copolymerized with difunctional monomers, and the protein is incorporated into a hyperbranched structure or a nanogel.

In yet another embodiment, the polymer employed in the protein-polymer composition can be degradable. In one non-limiting exemplary embodiment, a single linkage point between the protein and the polymer network can allow the protein to be efficiently released from the conjugated polymer by cleaving a degradable link, e.g. disulfide or acetal, as each protein is attached to the network through only one link/chain, thereby making these protein-polymer conjugates better suited for controlled release applications. In another non-limiting exemplary embodiment, multiple linkage points between the protein and the polymer network can provide additional control over efficiently releasing the conjugated polymer by cleaving the degradable linkages.

In an exemplary embodiment, an injectable protein-nanogel is prepared when copolymerization is conducted in an emulsion. (Scheme 1, FIG. 2)

In another embodiment, a protein-polymer nanogel hybrid is provided having a protein linked to one primary polymer chain at a precise region of the protein, thereby providing greater scaffold structural integrity whilst still forming well defined particles due to the emulsion process employed for the synthesis of the nanogel.

In additional embodiments, a targeted protein-polymer nanogel system is prepared using programmable behaviors of thermo-responsive or a pH sensitive composite structure. For example, as an exemplary embodiment, hydroxyethylmethacrylate (HEMA) can be chosen as a monomer for the polymerization process to provide available functional groups for further post-polymerization reactions and give a route for hydrogel synthesis.

In another exemplary embodiment, the polymer can be a cross-linked polymer. In such an embodiment, a degradable crosslinker can be used in the synthesis, which results in the preparation of nanogels that provide for a controlled release of proteins and bio-active molecules. Exemplary embodiments include, but are not limited to, deliveries of polynucleotides (e.g. oligonucleotides) and/or other therapeutic agents from the protein-polymer hybrids. This can be important for drug delivery applications through extended t½ life circulation of protein therapeutics.

In yet another embodiment, protein-polymer hybrids can incorporate different proteins at have synergistic activity, and can provide multi-protein nanogels with distinct protein domains within the nanogel. These systems have greater stability to enzymatic degradation while providing for controlled release of tethered bio-active agents if degradable cross-linkers are used, and also can have increased stability in organic solvents as compared to isolated wild-type proteins or wild-type proteins simply entrapped in a nanogel. Scheme 1 and FIG. 2 show an exemplary embodiment having a protein incorporated into a nanogel. These systems are proposed to have greater stability to enzymatic degradation, and increased potential for controlled release if degradable cross linkers are employed.

Another aspect of the invention is a method for preparing a protein-polymer composition having a protein with a site-specifically incorporated unnatural amino acid covalently attached to a polymer. The method comprises the steps of:

Providing a first protein containing a site specifically incorporated unnatural amino acid initiator, a polymerization catalyst precursor, and an organic solvent to an aqueous solution to form an emulsion;

providing a first radically polymerizable monomer to the emulsion; and providing a catalyst precursor reducing agent is added to the emulsion.

The process is exemplified by using a protein with a site-specifically incorporated unnatural amino acid with a CRP initiator functionality. Exemplary embodiments include, but are not limited to, CRP initiators for ATRP, NMP, or RAFT. These initiators can be introduced into nearly any protein thereby providing the ability to advance the field of protein polymer hybrids from non-functional proteins, e.g. bovine serum albumin, towards enzymes or therapeutically relevant systems. Therefore, one can assay the efficacy of the system and properly study the effects of polymer placement using commercially available enzyme assays.

In an embodiment, the method is exemplified by an unnatural amino acid initiator of formula 2, wherein R1 and R2 are independently H, C1-C8 alkyl, cycloalkyl, heterocycloalkyl, aryl, or heteroaryl; X is F, Cl, Br, I, $N_3$, alkoxyamine, or a thiocarbonyl thio moiety; A is O, S, or NR, wherein R is H, C1-C8 alkyl, cycloalkyl, heterocycloalkyl, aryl, or heteroaryl; and n is 0, 1, 2, or 3; or a salt thereof.

In another embodiment of the method, the unnatural amino acid initiator is of formula 1, wherein X is a F, Cl, Br, I, or —$N_3$, or a salt thereof. In yet another embodiment of the method, the unnatural amino acid initiator is of formula 1, wherein X is —$N_3$, or a salt thereof. In another embodiment of the method, the unnatural amino acid initiator is of formula 1, wherein X is Br or Cl, or a salt thereof.

In one embodiment, a coinitiator is added to the emulsion. In an additional embodiment, polyethyleneglycolisobutyryl bromide is a coinitiator and is added to the emulsion. In another embodiment, a second protein containing a site-specifically incorporated unnatural amino acid initiator is added to the emulsion.

In another embodiment, the polymerization catalyst precursor is a transition metal and a transition metal ligand species, that form a partially soluble transition metal complex that participates in a reversible redox reaction with the added initiator to form an active species suitable for polymerization of a radically polymerizable monomer. In an exemplary embodiment, the polymerization catalyst precursor comprises a copper halide and a transition metal ligand species. In another exemplary embodiment, the copper halide is $CuBr_2$ or $CuCl_2$.

Exemplary examples of radically polymerizable monomers include, but are not limited to methacrylates, acrylates, acrylamides, styrenics, or acrylamide-styrenics, or combinations thereof. In one embodiment, the method further comprises adding a radically polymerizable copolymer to the emulsion. The radically polymerizable copolymer can have repeating monomers. In an embodiment, the copolymer monomers can include methacrylates, acrylates, acrylamides, styrenics, or acrylamide-styrenics, or combinations thereof. In another embodiment, the polymer is copolymerized with difunctional monomers. In another embodiment, the first radically polymerizable monomer is added to the emulsion continuously or in stages during the polymerization process. In another embodiment, the radically polymerizable copolymer is added to the emulsion continuously or in stages during the polymerization process.

A catalyst precursor reducing agent for CRP reactions may be any reducing agent capable of reducing the transition metal catalyst from a higher oxidation state to a lower oxidation state, such as, but not limited to, ascorbic acid or salts thereof; tin octonate, reducing sugars such as fructose, antioxidants, those used in food preservatives such as flavonoids, beta carotene, α-tocopherol, propyl or octyl gallate (triphenol) BHA or BHT, or other food preservatives such as nitrites, propionic acids, sorbates, or sulfites. In another embodiment, the catalyst precursor reducing agent is ascorbic acid.

In another embodiment, the method further comprises the step of adding a cross-linking reagent to the emulsion. Exemplary example of a cross-linking reagent include, but are not limited to methacrylates, acrylates, acrylamides, styrenics, or acrylamide-styrenics, or combinations thereof. In another embodiment, when a cross-linking reagent is added to the emulsion, a coinitiator is further added to the emulsion.

To demonstrate the utility of a protein-polymer hybrid having a site-specifically incorporated unnatural amino acid covalently attached to a polymer, a green fluorescent protein ("GFP") with the functional initiating site specifically incorporated on sample GFP-1's surface was produced as a non-limiting exemplary protein. See scheme 2, FIG. 8. Using an exemplary unnatural amino acid, 4-(2'-bromoisobutylamido)-phenylalanine, GFP-1 was produced by replacing GFP-wt's Asp-134 through a variation of the procedure disclosed in U.S. Pat. No. 7,776,535, which is incorporated by reference. Specifically, the exemplary unnatural amino acid was incorporated into a *methanococcus jannaschii* (Mj) tyrosyltRNA synthetase (RS)/tRNACUA pair to genetically encode this initiator in response to an amber codon. Grafting from the incorporated 4-(2'-bromoisobutylamido)-phenylalanine initiator under standard ATRP conditions with the monomer oligo(ethylene oxide) monomethyl ether methacrylate, did not affect the green fluorescent properties of the GFP protein, allowing the fluorescent properties to be a measure of the influence of the conditions employed for the CRP on the structure of the selected protein. FIG. 1 shows that the fluorescent properties were not affected. Polymers grown from random sites on an unmodified sample of GFP-wt resulted in a lack of fluorescent properties by the GFP-polymer hybrid.

The exemplary GFP-1 proteins used in this work were attached to a polymer by a single covalent linkage to the site-specifically incorporated initiator, and the GFP-1 was incorporated into the resulting nanogel. The nanogel incorporated GFP-1 protein was not compromised by either the covalent unnatural amino acid-polymer linkage or subsequent incorporation into a nanogel, which was confirmed by the fact that the nanogels retained GFP's intrinsic light emitting properties, FIG. 3.2.

Other embodiments of the invention include the production of functional protein-polymer hybrid materials such as enzymes and assaying their activity under synthetically relevant conditions. This ability to prepare functional proteins with site selected functionality is further exemplified by preparation of a Catalase that was bio-engineered to possess 4 ATRP initiating groups, sample Cat-1 FIG. 2. Catalase is an enzyme that converts $H_2O_2$ into oxygen and water and it was confirmed that the enzymatic reaction was not modified after the Catalase had undergone polymer modification, Image 1, FIG. 6.

One skilled in the art should appreciate that the above steps are merely exemplary and used to enable one skilled in the art to prepare protein-polymer compositions containing a protein with site-specifically incorporated unnatural amino acid covalently attached to a polymer, Additionally, those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto.

EXAMPLES

Example 1: Synthesis of Protein-Polymer Conjugates Via "Grafting from" an Incorporated Functionality The procedure used to incorporate a functional group that can act as an initiator for an ATRP into a protein is schematically represented in Scheme 3, FIG. 9. The first formed ATRP initiator 4-(2'-bromoisobutyramido) phenylalanine (1) need not be asymmetric, since the MjRS utilizes only the L form. (B, FIG. 9.2).

This was accomplished using an *E. coli* tyrosyl tRNA/tRNA-synthesize pair vector. By using genetic engineering, specific placement of the initiating amino acid was selected to be expressed at the 134 position of GFP, the resulting modified protein being GFP-1, protecting the protein's active sites and structurally weak regions.

N-Boc-4-(2'-bromoisobutyramido)-phenylalanine

Commercially obtained N-Boc-4-aminophenylalanine (3.62 g, 0.01447 mol) was dissolved in 50 mL of dry THF, 2-bromoisobutyryl bromide (1.757 mL, 0.01422 mol) was added dropwise over 30-60 seconds with vigorous stirring. The reaction was complete after 10 min (monitored by TLC). After approximately 20 min. the entire reaction mixture (including newly formed precipitate) was transferred to a separatory funnel with $CHCl_3$, and approximately 100 mL of $H_2O$. The reaction mixture was extracted with $CHCl_3$ (3×50 mL). The organic phase was washed with distilled water (2×50 mL) and brine (50 mL). The organic phase was dried with $MgSO_4$ and evaporated in vacuo to obtain the crude product (4.55 g). The crude solid product was recrystallized in 20-30 acetonitrile three times to purify the product. After three recrystallizations, the desired product was obtained in 65% yield (3.63 g). $^1$H NMR (500 MHz, DMSO) confirmed the structure.

4-(2'-bromoisobutyramido)phenylalanine

N-Boc-4-(2'-bromoisobutyramido)-phenylalanine (4.8 g, 0.0112 mol) was dissolved in 50 mL ethyl acetate under argon and dry 4 M HCl in dioxane (50 mL) was subsequently added to the solution while stirring at room temperature overnight. The reaction mixture was then evaporated under reduced pressure to a final volume of 5-10 mL. Pentane was then added to the solution, and the precipitate was filtered using an M type filter crucible and dried under reduced pressure. The product was present as the HCl salt in 97% yield (3.93 g). $^1$H NMR (500 MHz, DMSO) confirmed the structure.

Selection of an Aminoacyl-tRNA Synthetase Specific for 4-(2'-bromoisobutyramido)phenylalanine The library of aminoacyl-tRNA synthetases was encoded on a kanamycin (Kn) resistant plasmid (pBK, 3000 bp) under control of the constitutive *Escherichia coli* GlnRS promoter and terminator. The aminoacyl synthetase library (3D-Lib) was randomized as follows: Leu65, His70, Gln155, and Ile159 were randomized to all 20 natural amino acids; Tyr32 was randomized to 15 natural amino acids (less Trp, Phe, Tyr, Cys, and Ile); Asp158 was restricted to Gly, Ser, or Val; Leu162 was restricted to Lys, Ser, Leu, His, and Glu; and Phe108 and Gln109 were restricted to the pairs Tip-Met, Ala-Asp, Ser-Lys, Arg-Glu, Arg-Pro, Ser-His, or Phe-Gln. The library plasmid, pBK-3D-Lib, was moved between cells containing a positive selection plasmid (pCG) and cells containing a negative selection plasmid (pNEG).

The positive selection plasmid, pCG (10000 bp), encodes a mutant *Methanococcus jannaschii* (Mj) tyrosyl-tRNACUA, an amber codon-disrupted chloramphenicol acetyltransferase, an amber codon-disrupted T7 RNA polymerase that drives the production of green fluorescent protein, and the tetracycline (Tet) resistance marker. The negative selection plasmid, pNEG (7000 hp), encodes the mutant tyrosyl-tRNACUA, an amber codon-disrupted barnase gene under control of an arabinose promoter and rrnC terminator, and the ampicillin (Amp) resistance marker. pCG electrocompetent cells and pNEG electrocompetent cells were made from DH10B cells carrying the respective plasmids and stored in 100 µL aliquots at −80° C. for future rounds of selection.

The synthetase library in pBK-3D-Lib was transformed by electroporation into DH10B cells containing the positive selection plasmid, pCG. The resulting pCG/pBK-3D-Lib-containing cells were amplified in 1 L of 2×YT with 50 µg/mL Kn and 25 µg/mL Tet with shaking at 37° C. The cells were grown to saturation, then pelleted at 5525 ref, resuspended in 30 mL of 2×YT and 7.5 mL of 80% glycerol, and stored at −80° C. in 1 mL aliquots for use in the first round of selections.

For the first positive selection, 2 mL of pCG/pBK-3D-Lib cells were thawed on ice before addition to 1.2 L of room temperature 2×YT media containing 50 µg/mL Kn and 25 µg/mL Tet. After incubation (11 h, 250 rpm, 37° C.), a 200 µL aliquot of these cells was plated on eleven 15 cm GMML-agar plates containing 50 µg/mL Kn, 25 µg/mL Tet, and 60 µg/mL, chloramphenicol (Cm). The positive selection agar medium also contained 1 mM 1. After spreading, the surface of the plates was allowed to dry completely before incubation (37° C., 15 h). To harvest the surviving library members from the plates, 10 mL of 2×YT (50 µg/mL Kn, 25 µg/mL Tet) was added to each plate. Colonies were scraped from the plate using a glass spreader. The resulting solution was incubated with shaking (60 min, 37° C.) to wash cells free of agar. The cells were then pelleted, and plasmid DNA was extracted. For the first positive selection a Qiagen midiprep kit was used to purify the plasmid DNA. For all other plasmid purification steps a Qiagen miniprep kit was used to purify the plasmid DNA. The smaller pBK-3D-Lib plasmid was separated from the larger pCG plasmid by agarose gel electrophoresis and extracted from the gel using the Qiagen gel extraction kit.

The purified pBK-3D-Lib was then transformed into pNEG-containing DH10B cells. A 100 µL sample of pNEG electrocompetent cells was transformed with 50 ng of purified pBK-3D-Lib DNA. Cells were rescued in 1 mL of SOC for 1 h (37° C., 250 rpm) and the entire 1 mL of rescue solution was plated on three 15 cm LB plates containing 100 µg/mL Amp, 50 µg/mL Kn, and 0.2% L-arabinose. Cells were collected from plates and pBK-3D-Lib plasmid DNA was isolated in the same manner as described above for positive selections.

For the second round of positive selection, 50 ng of purified library DNA was transformed into 100 µL of pCG competent cells. The transformants were rescued for 1.5 h in 1 mL of SOC (37° C., 250 rpm). A 50 sample of these cells was plated on three plates prepared as described in the first positive selection on LB agar plates.

For the second negative selection, one plate was spread with 250 µL of rescued cells, and two plates were spread with 50 µL of rescued cells and then incubated (12-16 h, 37° C.). For this round, the cells were plated on LB agar containing 100 µg/mL Amp, 50 µg/mL Kn, and 0.04% L-arabinose.

In order to evaluate the success of the selections based on variation in synthetase efficacy (as opposed to traditional survival/death results), the synthetases resulting from the selection rounds were tested with the pALS plasmid. This plasmid contains the sfGFP reporter with a TAG codon at residue 150 as well as tyrosyl-tRNACUA. When a pBK plasmid with a functional synthetase is transformed with the pALS plasmid and the cells are grown in the presence of the appropriate amino acid on autoinduction agar, sfGFP is expressed and the colonies are visibly green.

One microliter of each library resulting from the second positive and the second negative rounds of selection was transformed with 60 µL, of pALS-containing DH10B cells. The cells were rescued for 1 hr in 1 mL of SOC (37° C., 250 rpm). A 250 µL and 50 µL of cells from each library were plated on autoinducing minimal media with 25 µg/mL Kn, 25 µg/mL Tet, and 1 mM 1. Plates were grown at 37° C. for 24 hours and then grown on the bench top, at room temperature, for an additional 24 hours.

Autoinducing agar plates were prepared by combining the reagents in Table 1A with an autoclaved solution of 40 g of agarose in 400 mL water. Sterile water was added to a final volume of 500 mL. Antibiotics were added to a final concentration of 25 µg/mL Tet and 25 µg/mL Kan. Nine plates were poured with 1 mM 1, and nine plates were maintained as controls without UAA.

A total of 92 visually green colonies were selected from the two 1 mM 1 plates and used to inoculate a 96-well plate containing 0.5 mL per well non-inducing minimal media (Table 1B, with sterile water added to a final volume of 500 mL) with 25 µg/mL Kn, 25 µg/mL Tet. After 24 hours of growth (37° C., 250 rpm), 5 µL of these non-inducing samples were used to inoculate 96-well plates with 0.5 mL autoinduction media (Table 1C, with sterile water added to a final volume of 500 mL) containing 25 µg/mL Kn, 25 µg/mL Tet with and without 1 mM 1. Fluorescence measurements of the cultures were collected 40 hours after inoculation using a HORIBA Jobin Yvon FluoroMax®-4. The emission from 500 to 520 nm (1 nm bandwidth as summed with excitation at 488 nm (1 nm bandwidth). Samples were prepared by diluting suspended cells directly from culture 100-fold with phosphate buffer saline (PBS).

TABLE 1

Components for autoinducing and non-inducing mediums, for final volume of 500 mL.

| | A) Auto-induction medium | B) Non-inducing medium | C) Auto-inducing plates |
|---|---|---|---|
| 5% aspartate, pH 7.5 | 25 mL | 25 mL | 25 mL |
| 10% glycerol | 25 mL | | 25 mL |
| 25× 18 amino acid mix | 20 mL | 20 mL | 20 mL |
| 50× M | 10 mL | 10 mL | 10 mL |

TABLE 1-continued

Components for autoinducing and non-inducing mediums, for final volume of 500 mL.

| | A) Auto-induction medium | B) Non-inducing medium | C) Auto-inducing plates |
|---|---|---|---|
| leucine (4 mg/mL), pH 7.5 | 5 mL | 5 mL | 5 mL |
| 20% arabinose | 1.25 mL | — | 1.25 mL |
| 1M MgSO$_4$ | 1 mL | 1 mL | 1 mL |
| 40% glucose | 625 μL | 6.25 mL | 125 μL |
| Trace metals | 100 μL | 100 μL | 100 μL |

Fluorescence measurements of 92 synthetases with GFP clones were conducted. Expressions of 500 μL were grown for 40 hours before dilution of suspended cells directly from culture 100-fold with phosphate buffer saline (PBS). Fluorescence measurements were collected using a HORIBA Jobin Yvon FluoroMax®-4. The emission from 500 to 520 nm (1 nm bandwidth) was summed with excitation at 488 nm (1 nm bandwidth).

Fluorescence Analysis of Highest-Fluorescing Clones

Non-inducing cultures (3 mL) with 25 μg/mL Kn and 25 μg/mL Tet were grown to saturation (37° C. with shaking at 250 rpm) from the 20 highest-fluorescing colonies. Autoinduction cultures (3 mL) with 25 μg/mL Kn and 25 μg/mL Tet were inoculated with 30 μL of non-inducing cultures and grown with and without 1 mM 1 at 37° C. with shaking at 250 rpm. After approximately 40 hours, fluorescence was assessed. The top eight performing clones were sequence revealing five unique members. The top performing clone (G2) was moved from the pBK-G2 plasmid to the pDule plasmid (PDule-BIBAF). pDule plasmid was generated by amplifying the MjYRS gene from the pBK plasmid isolated from the library using primers RSmovef (5'-CGCGCGC-CATGGACGAATTTGAAATG-3') and RSmover (5'-GACTCAGTCTAGGTACCCGTTTGAAACTGCAGT-TATA-3'). The amplified DNA fragments were cloned in to the respective sites on the pDule plasmids using the incorporated NcoI and KpnI sites.

Expression and Purification of GFP-1.

DH10B E. coli cells co-transformed with the pBad-sfGFP-134TAG vector and the machinery plasmid pDule-BIBAF were used to inoculate 5 mL of non-inducing medium containing 100 μg/mL Amp and 25 μg/mL Tet. The non-inducing medium culture was grown to saturation with shaking at 37° C., and 5.0 mL was used to inoculate 0.5 L autoinduction medium with 100 μg/mL Amp, 25 μg/mL Tet, and 1 mM 1 (0.5 L of media grown in 2 L plastic baffled flasks). After 40 hours of shaking at 37° C., cells were collected by centrifugation.

The protein was purified using BD-TALON cobalt ion-exchange chromatography. The cell pellet was resuspended in wash buffer (50 mM sodium phosphate, 300 mM sodium chloride, pH 7) containing 1 mg/mL chicken egg white lysozyme, and sonicated 3×1 min while cooled on ice. The lysate was clarified by centrifugation, applied to 6-9 mL bed-volume resin, and bound for 30 min. Bound resin was washed with >50 volumes wash buffer.

Protein was eluted from the bound resin with 2.5 mL aliquots of elution buffer (50 mM sodium phosphate, 300 mM sodium chloride, 150 mM imidazole pH 7) until the resin turned pink and the color of the eluent the column was no longer green. The elusions concentrations were check with a Bradford protein assay. The protein were desalted into PBS using PD10 columns and concentrated with 3000 MWCO centrifuge filters.

Figure 8:
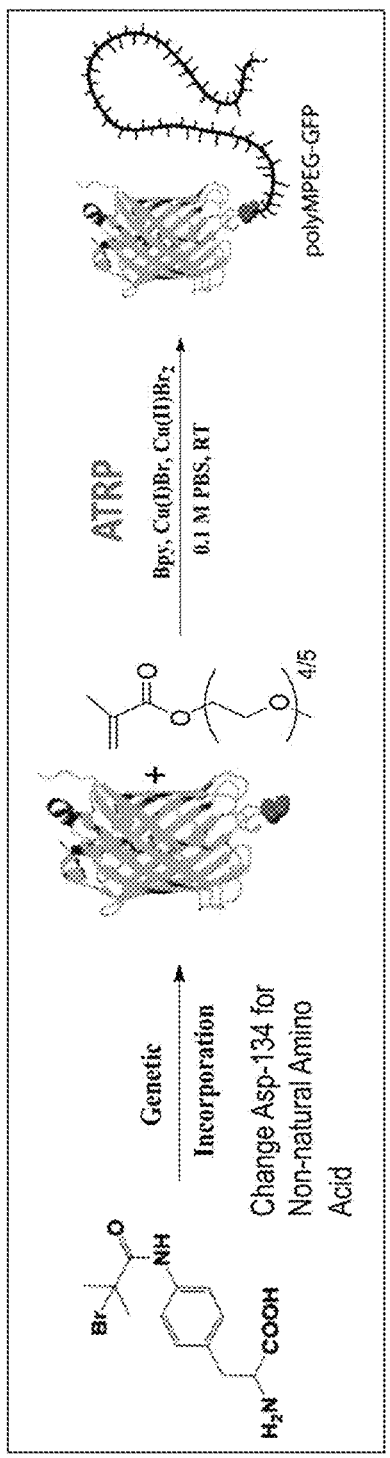
FIG. 8: Shows "Grafting From" GFP-1, where an exemplary unnatural amino acid, 4,(2'-bromoisobutylamido)-phenylalanine, was produced by replacing GFP-wt's Asp-134 (Synthetic Scheme 2).

The location of incorporation of 1 at site D134 in GFP protein is indicated by the space-filling amino acid (previously Asp) in Scheme 2, FIG. 8. Altering the amino acid at site 134 in a flexible loop unconnected to the chromophore does not affect the stability or fluorescence of GFP.

MS analysis of GFP-1 confirmed the efficient high fidelity incorporation of a single unit of 4-(2'-bromoisobutyramido) phenylalanine into GFP in response to an amber stop codon. ESI-MS-T of analysis of sfGFP shows a single major peak at 27827.0 Da±1 Da while ESI-MS-T of analysis of GFP-1 shows a single major peak at 28024.0 Da±1 Da. This shows the expected molecular weight difference of 197 Da from native GFP indicating a single efficient incorporation of 4-(2'-bromoisobutyramido)phenylalanine at the expected site. Each sample did show a small peak at −131±1 Da indicating minor amounts of peptidase-based removal of N-terminal methionines and +22 sodium adducts. No other peaks were observed that would correlate with background incorporation of a natural amino acid.

In summary, the evolved MjRS/tRNACUA pair in pDule-BIBAF allows for site-specific incorporation of 1 in response to an amber codon. The image in Scheme 3, FIG. 9 shows expression levels of GFP-wt from pBad-GFP-His6. Production of GFP-1 from pBad-GFP-134TAG-His6 is dependent on 1 in the growth media: lane 3 without 1 present, lane 4 with 1 mM 1 present. The functional protein was purified by Co2+ affinity chromatography, separated by SDS-PAGE, and stained with Coomassie.

ATRP Reactions Grafting from GFP-wt and GFP-1.
GFP-wt.

Initiator stock solution: Bpy (16.70 mg, 1.07×10$^{-3}$ mmol) and Cu(II)Br$_2$ (6 mg, 2.68×10$^{-4}$ mmol) were dissolved in 10 mL of H$_2$O; the solution was deoxygenated with nitrogen. Cu(I)Br (3.8 mg, 2.68×10$^{-4}$ mmol) was added to the mixture. Monomer, OEO$_{300}$MA (21 mg, 6.9×10$^{-2}$ mmol) was added to 100 μL of GFP-wt (10.2 mg, 3.4×10$^{-2}$ mmol). This solution was deoxygenated with nitrogen for 20 min. and then degassed initiator solution (250 μl) was added to the reaction mixture. The zero time sample was removed and the reaction was sealed and mixed for 3 hours then quenched by exposure to air. There was no difference between GPC traces from first sample and final sample indicating that no grafting from reaction occurred.

GFP-1.

Figure 4:
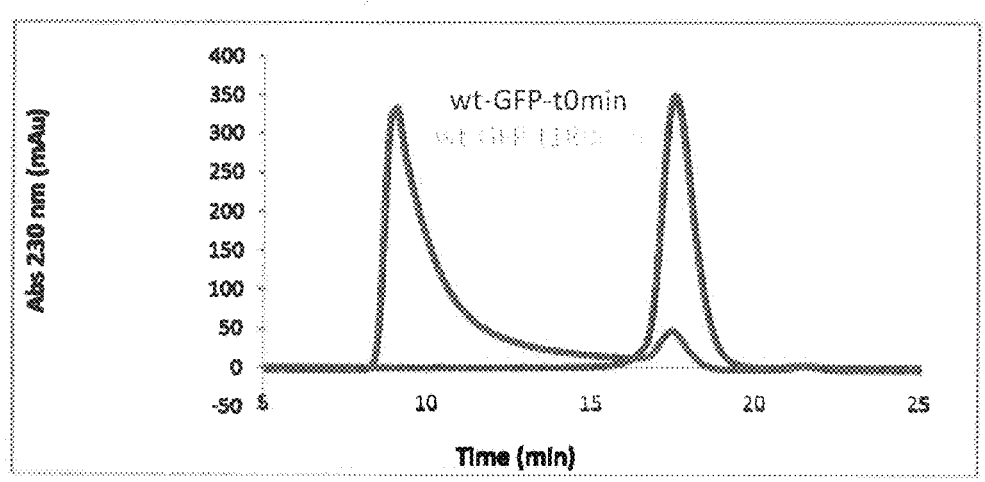
FIG. 4: Fast Protein Liquid Chromatography ("FPLC") of GFP-1 reaction, GFP-1 (0 min), GFP-1-p(OEO300MA) (180 min).

Initiator stock solution: Bpy (16.70 mg, 1.07×10$^{-3}$ mmol) and Cu(II)Br$_2$ (6 mg, 2.68×10$^{-4}$ mmol) were dissolved in 10 mL of H$_2$O; the solution was deoxygenated with nitrogen. Cu(I)Br (3.8 mg, 2.68×10$^{-4}$ mmol) was added to the mixture. Monomer, OEO$_{300}$MA (10 mg, 3.42×10$^{-2}$ mmol) was added to 100 of GFP-1 (6 mg, 2.14×10$^{-4}$ mmol). This solution was deoxygenated with nitrogen for 20 min. then degassed initiator solution (100 μL) was added to the reaction mixture. The reaction was sealed and mixed for 3 hours then quenched by exposure to air. The production of GFP-1-p(OEO300MA) was confirmed by FPLC SEC analysis and SDS-PAGE. The reaction appeared to have high initiator efficiency, above 95%, as indicated by the area under the curve for the residual GFP-1 in the GFP-p (OEO300MA) sample taken after 180 min, FIG. 4. As can clearly be seen there is a tailing towards low Mn region of the elutogram. The primary issue seems to be poor deactivation since changing the monomer concentration from ~35% to ~4% in aqueous solutions a tail towards low Mn forms in the low monomer concentration case.

These protein-polymer hybrids were analyzed using dynamic light scattering, UV-visible fluorescence spectroscopy and confocal microscopy to confirm the successful incorporation of the protein into the hybrid while preserving its tertiary structure, FIG. 3.2.

Confirmation of Preparation of a Thermoresponsive Protein-Polymer Hybrid.

Figure 5:
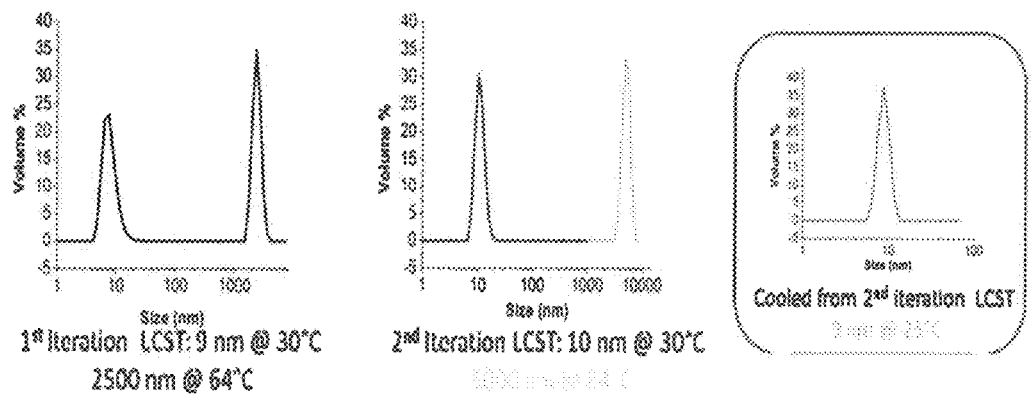
FIG. 5: Lower Critical Solution Temperature ("LCST") behavior of GFP-1-p (OEO300MA)

An interesting phenomenon that is observed with the p(OEO$_{300}$MA) polymers is their LCST behavior at ~64° C. To determine if the GFP-1-p(OEO$_{300}$MA) hybrids retained this property dynamic light scattering (DLS) was employed to study the thermal response of the system. Setting the temperature to 25° C. and raising the temperature in 1° C. steps a distinct transition from 10 nm (GFP-1-p (OEO$_{300}$MA)) to micron sized particles was clearly observed at 64° C. The GFP-1-p(OEO$_{300}$MA) retained its initial size after cooling to room temperature after 2 iterations of LEST, FIG. 5. This exemplary thermoresponsive phenomenon of the protein-polymer conjugate can be made more powerful when hybrid structures with biologically relevant LCST temperature are prepared by copolymerization procedures for potential controlled release applications.

Example 2: Synthesis of a Protein-g-Polymer Nanogels

In order to exemplify another embodiment, cationic nanogels were prepared by ATRP in an inverse mini-emulsion in order to improve control over particle size and prepare functional nanogels between 50 and 200 nm in diameter. Incorporation of a degradable crosslinker allows bio-degradation of the crosslinkage and release of encapsulated biomolecules and colloidal stability. Particle size was measured using a Zetasizer Nano from Malvern Instruments. Confocal microscopy was carried out using a Carl Zeiss LSM 510 Meta NLO Confocor 3 Inverted Spectral Confocal Microscope using an excitation of 488 nm. UV-vis spectroscopy was conducted on a Cary 5000 spectrophotometer and fluorescence spectra were collected on a Cary Eclipse fluorescence spectrophotometer.

GFP-NG

To prepare the water phase of an inverse miniemulsion ATRP Cu(II)Br$_2$ (2.79 mg, 0.013 mmol) TPMA catalyst (3.63 mg, 0.013 mmol), 4% (w/w total solids) GFP-1 (52.5 mg, 0.002 mmol), PEO$_{2000}$iBBr (50 mg, 0.025 mmol) a co-initiator, oligo(ethylene oxide)$_{300}$methacrylate (OEO$_{300}$MA) (900 mg, 3 mmol), as a monomer, and PEO$_{4000}$dimethacrylate (400 mg, 0.1 mmol) as a crosslinking agent were dissolved in 1.46 ml 0.1M PBS buffer pH 7.4 and emulsified with a 0.05% (w/w) of span-80 in cyclohexane using ultra sonication to form stable droplets ~200 nm size. After degassing, ascorbic acid was injected to reduce the Cu(II)Br$_2$ to Cu(I)Br and initiate polymerization which was stopped after 15 hours stirring at 30° C. The nanogels were purified by precipitation by addition of the emulsion into THF followed by extensive dialysis (50000 MWCO membrane) into water to remove unreacted reagents. Dynamic light scattering of GFP1-NG peak showed that the particle size ~240 nm and confocal microscopy of GFP1-NG showed that the nanoparticles retained their fluorescent properties, FIG. 3.2.

Catalase-NG (FIG. 2)

Catalase is an enzyme that converts H$_2$O$_2$ into oxygen and water. A catalase enzyme that was been engineered with 4 ATRP initiating groups, (Cat-1), was employed as one of two different initiators, the other was a mono-functional PEG based MI, in an ATRP of PEO300MA and a PEG based crosslinker, PEG$_{4000}$DM, to prepare an enzyme-g-PEG conjugate nanoparticle that was evaluated as a reducing agent.

PEO$_{2000}$-iBBr (56 mg, 0.028 mmol), 238-catalse-initiator (6.3 mg, 0.018 μM 0.06 mol %, 4 weight %) OEO$_{300}$MA (1008 mg, 3.36 mmol), PEG$_{4000}$DM (448 mg, 0.11 mmol), CuBr$_2$ (3.12 mg, 0.014 mmol), TPMA (4.06 mg, 0.014 mmol) were dissolved in 1.46 ml of water in a 50 ml pear shaped flask. A 0.05 w/w % solution of Span-80 (1.46 g) in cyclohexane (29.26 g) was added to the reaction mixture and the solution was sonicated until a stable inverse miniemulsion was formed. The solution was degassed and 200 μL of degassed ascorbic acid in water (0.066 mg/ml) was added to activate the catalyst by reducing a fraction of the Cu$^{II}$/complex to Cu$^I$. After 15 hours the solid hybrid was precipitated by addition to THF, washed twice with THF and 3 times with water. The resulting nanogels were extensive purified using tangential flow filtration with a 300 kDa MWCO membrane.

In both the GFP-1 and Catalase 1 examples well defined protein nanogels were produced as measured by dynamic light scattering (DLS), FIG. 3.1. Confocal microscopy was used to study the structure of the GFP-nanogel due to intrinsic light emitting properties of the GFP, FIG. 3.2, to determine the structural integrity of the protein within the greater nanogel matrix. The retention of the fluorescent properties indicate that proteins can be subjected to grafting from reaction while retaining their shape and biological activity The Catalase-nanogel could be studied by testing the activity of this enzyme by exposing it to H$_2$O$_2$ to show that it retained catalytic activity. When hydrogen peroxide was added to an aqueous solution of the nanogels there was an immediate evolution of oxygen, see Image 1, FIG. 6.

The primary issue in both of the protein nanogels synthesis was the possibility that free protein was present in the system. To determine if any free protein is remaining a through purification was conducted on these systems followed by a leaching assay to determine how much protein is released into the supernatant liquid. A protein will be considered to be covalently incorporated if after extensive washing a constant absorbance in the nanogels is observed.

For more conclusive proof of protein incorporation into a nanogel the application of degradable crosslinkers can be applied. Considering the case of Cat-NG the free Catalase can easily become trapped into the nanogel while the Cat-1 will be covalently attached. The use of degradable crosslinkers during the synthesis of allows stable nanogels to be synthesized purified and then degraded. After degradation the nanogels synthesized with Cat-1 should contain peaks for the protein-polymer hybrid while the nanogels synthesized with Cat-wt should contain only peaks for Cat-wt.

What is claimed is:

1. A protein-polymer composition comprising:

a first protein with a site-specifically incorporated unnatural amino acid having a covalently attached polymer, wherein the unnatural amino acid is represented by formula 2:

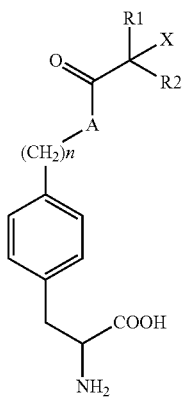

wherein R1 and R2 are independently H, C1-C8 alkyl, cycloalkyl, heterocycloalkyl, aryl, or heteroaryl; X is F, Cl, Br, I, $N_3$, alkoxyamine, or a thiocarbonyl thio moiety; A is O, S, or NR, wherein R is H, C1-C8 alkyl, cycloalkyl, heterocycloalkyl, aryl, or heteroaryl; and n is 0, 1, 2, or 3; or a salt thereof.

2. The protein-polymer composition of claim 1, wherein the unnatural amino acid is site specifically incorporated into the protein one to five times.

3. The protein-polymer composition of claim 1, wherein the incorporated unnatural amino acid is an initiator for a controlled radical polymerization reaction.

4. The protein-polymer composition of claim 3, wherein the incorporated unnatural amino acid is an initiator for atom transfer radical polymerization.

5. The protein-polymer composition of claim 1, wherein the unnatural amino acid is represented by formula 2:

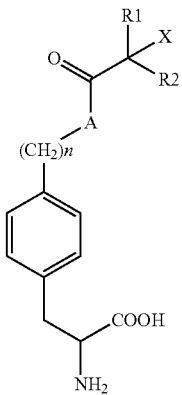

wherein R1 and R2 are independently H, C1-C8 alkyl, cycloalkyl, heterocycloalkyl, aryl, or heteroaryl; X is F, Cl, Br, I, $N_3$, or alkoxyamine; A is O, S, or NR, wherein R is H, C1-C8 alkyl, cycloalkyl, heterocycloalkyl, aryl, or heteroaryl; and n is 0, 1, 2, or 3; or a salt thereof.

6. The protein-polymer composition of claim 5, wherein the unnatural amino acid is represented by formula 1:

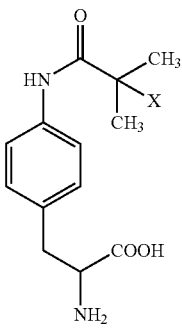

wherein X is a F, Cl, Br, I, or —$N_3$, or a salt thereof.

7. The protein-polymer composition of claim 6, wherein X is —$N_3$, or a salt thereof.

8. The protein-polymer composition of claim 6, wherein X is Br or Cl, or a salt thereof.

9. The protein-polymer composition of claim 1, wherein the polymer comprises an incorporated cross-linking moiety.

10. The protein-polymer composition of claim 9, wherein the cross-linking moiety comprises a polymerizable group.

11. The protein-polymer composition of claim 1, wherein the polymer is degradable.

12. The protein-polymer composition of claim 1, wherein the polymer comprises repeating units.

13. The protein-polymer composition of claim 12, wherein the repeating units are selected from the group comprising methacrylates, acrylates, acrylamides, styrenics, and acrylamide-styrenics, or combinations thereof.

14. The protein-polymer composition of claim 1, wherein the polymer comprises a copolymer.

15. The protein-polymer composition of claim 14, wherein the copolymer comprises repeating units.

16. The protein-polymer composition of claim 15, wherein the repeating units are selected from the group comprising methacrylates, acrylates, acrylamides, styrenics, and acrylamide-styrenics, or combinations thereof.

17. The protein-polymer composition of claim 1, comprising a second protein with a site-specifically incorporated unnatural amino acid having a covalently attached polymer.

18. A method for preparing a protein-polymer composition comprising the steps of:
providing a first protein containing a site specifically incorporated unnatural amino acid initiator, wherein the unnatural amino acid is represented by formula 2:

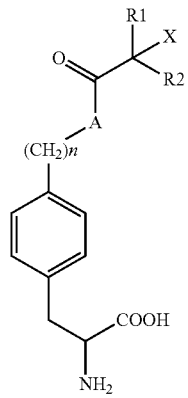

wherein R1 and R2 are independently H, C1-C8 alkyl, cycloalkyl, heterocycloalkyl, aryl, or heteroaryl; X is F, Cl, Br, I, N₃, alkoxyamine, A is O, S, or NR, wherein R is H, C1-C8 alkyl, cycloalkyl, heterocycloalkyl, aryl, or heteroaryl; and n is 0, 1, 2, or 3; or a salt thereof, a polymerization catalyst precursor, and an organic solvent to an aqueous solution to form an emulsion;
providing a first radically polymerizable monomer to the emulsion; and
providing a catalyst precursor reducing agent to the emulsion under conditions suitable to initiate the controlled radical polymerization.

19. The method of claim 18, wherein the controlled radical polymerization is an atom transfer radical polymerization.

20. The method of claim 18, wherein the polymerization catalyst precursor is CuX' and a transition metal ligand species, wherein X' is —Cl₂ or —Br₂.

21. The method of claim 18, wherein the reducing agent is ascorbic acid or a salt thereof.

22. The method of claim 18, further comprising the step of:
adding a cross-linking agent to the emulsion.

23. The method of claim 22, wherein the cross-linking agent comprises methacrylates, acrylates, acrylamides, styrenics, or acrylamide-styrenics, or combinations thereof.

24. The method of claim 18, further comprising the step of:
adding a coinitiator to the emulsion.

25. The method of claim 24, wherein the coinitiator is polyethyleneglycolisobutyryl bromide.

26. The method of claim 18, wherein the unnatural amino acid initiator is represented by formula 2:

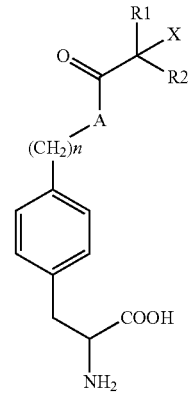

wherein R1 and R2 are independently H, C1-C8 alkyl, cycloalkyl, heterocycloalkyl, aryl, or heteroaryl; X is F, Cl, Br, I, N₃, alkoxyamine, or a thiocarbonyl thio moiety; A is O, S, or NR, wherein R is H, C1-C8 alkyl, cycloalkyl, heterocycloalkyl, aryl, or heteroaryl; and n is 0, 1, 2, or 3; or a salt thereof.

27. The method of claim 26, wherein the unnatural amino acid is represented by formula 1:

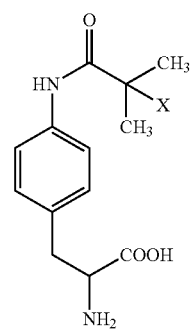

wherein X is a F, Cl, Br, I, or —N₃, or a salt thereof.

28. The method of claim 27, wherein X is —N₃, or a salt thereof.

29. The method of claim 27, wherein X is Br or Cl, or a salt thereof.

30. The method of claim 18, further comprising the step of:
adding a copolymer to the emulsion.

31. The method of claim 18, wherein the radically polymerizable monomer is added to the emulsion continuously or in stages during the polymerization process.

32. The method of claim 22, further comprising the step of:
adding a coinitiator to the emulsion.

33. The method of claim 18, further comprising the step of:
adding a second protein containing a site specifically incorporated unnatural amino acid initiator to the emulsion.

34. A protein-polymer composition comprising a first protein with a site-specifically incorporated unnatural amino acid having a covalently attached polymer, the unnatural amino acid is represented by formula 1:

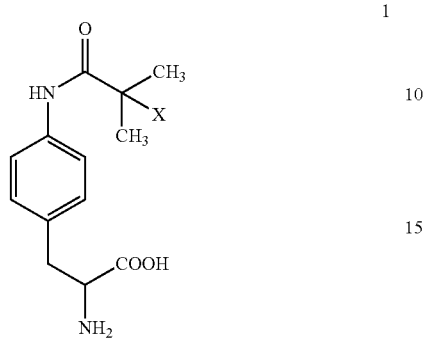

wherein X is —N₃, or a salt thereof.

35. The protein-polymer composition of claim 34 further comprising a second protein with a site-specifically incorporated unnatural amino acid having a covalently attached polymer.

36. The protein-polymer composition of claim 3, wherein the incorporated unnatural amino acid is an initiator for a controlled radical polymerization reaction and is introduced into the first protein from an orthogonal tRNA/amino acyl-tRNA synthase specific for the unnatural amino acid initiator.

* * * * *

SEQUENCE LISTING

<160> NUMBER OF SEQ ID NOS: 2

<210> SEQ ID NO 1
<211> LENGTH: 26

```
<212> TYPE: DNA
<213> ORGANISM: Escherichia coli

<400> SEQUENCE: 1
cgcgcgccat ggacgaattt gaaatg                                        26

<210> SEQ ID NO 2
<211> LENGTH: 37
<212> TYPE: DNA
<213> ORGANISM: Escherichia coli

<400> SEQUENCE: 2
gactcagtct aggtacccgt ttgaaactgc agttata                            37
```